(12) United States Patent
Craig et al.

(10) Patent No.: US 6,699,882 B2
(45) Date of Patent: Mar. 2, 2004

(54) PAROXETINE COMPOSITIONS

(75) Inventors: Andrew Simon Craig, Sevenoaks (GB); Neal Ward, Crowborough (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 10/134,917

(22) Filed: Apr. 29, 2002

(65) Prior Publication Data

US 2002/0123511 A1 Sep. 5, 2002

Related U.S. Application Data

(63) Continuation of application No. 09/646,622, filed as application No. PCT/GB99/00922 on Mar. 24, 1999, now abandoned.

(30) Foreign Application Priority Data

Mar. 24, 1998 (GB) .............................................. 9806312

(51) Int. Cl.[7] ............................................. A61K 31/445
(52) U.S. Cl. ........................................ 514/321; 546/197
(58) Field of Search ........................... 514/321; 546/197

(56) References Cited

U.S. PATENT DOCUMENTS

| | | | |
|---|---|---|---|
| 5,672,612 A | 9/1997 | Ronsen et al. | 514/317 |
| 5,811,436 A | 9/1998 | Leonard et al. | 514/321 |
| 5,955,475 A | 9/1999 | Krape et al. | 514/321 |
| 6,168,805 B1 | 1/2001 | Hein, II et al. | 424/465 |

FOREIGN PATENT DOCUMENTS

| | | |
|---|---|---|
| DE | 196 03 797 | 8/1996 |
| EP | 0 223 403 | 5/1987 |
| WO | WO-95/16448 | 6/1995 |
| WO | WO96/24595 | 8/1996 |
| WO | WO99/16440 | 4/1999 |
| WO | WO-99/16640 | 4/1999 |
| WO | WO-01/02393 | 1/2001 |

OTHER PUBLICATIONS

Nikolakakis et al. "Solid state adsorption of . . . " J. Pharmacol. v. 41, pp. 145–148 (1989).

Greenburg, CA 50:47302 (1956).

Unilever, CA 58:51848 (1962).

RN 61790–53–2, Celite.

*Primary Examiner*—Ceila Chang
(74) *Attorney, Agent, or Firm*—Wayne J. Dustman

(57) ABSTRACT

Paroxetine is adsorbed on a carrier to form a free-flowing powder useful for capsule filling or for tablet formulation; and used in therapy to treat depression.

1 Claim, No Drawings

PAROXETINE COMPOSITIONS

This is a continuation of application Ser. No. 09/646,622 filed Nov. 28, 2000, now abandoned which is a § 371 of PCT/GB99/00922, filed Mar. 24, 1999.

The present invention relates to new formulations of a pharmaceutically active compound, and in particular to a novel formulation of paroxetine.

Pharmaceutical products with antidepressant and anti-Parkinson properties are described in U.S. Pat. Nos. 3,912,743 and 4,007,196. An especially important compound among those disclosed is paroxetine, the (−)trans isomer of 4-(4'-fluorophenyl)-3-(3',4'-methylenedioxy-phenoxymethyl)-piperidine.

In the literature this compound is usually isolated as an acid salt, especially the hydrochloride. Paroxetine is approved for human use as the hydrochloride salt, and has been proposed for the treatment and prophylaxis of inter alia depression, obsessive compulsive disorder (OCD) and panic.

Paroxetine hydrochloride has been described in the literature as a crystalline hemihydrate (see EP-A-0223403 of Beecham Group) and as various crystalline anhydrate forms (see WO96/24595 of SmithKline Beecham).

Paroxetine free base has hitherto been disclosed in the literature as an oil, and so the free base has not itself been considered for therapeutic use, preference being given to crystalline forms which can be more easily purified and processes into dosage forms.

The present invention is based on the discovery that paroxetine, for example paroxetine free base, is advantageously formulated into pharmaceutical compositions when adsorbed on or absorbed by a solid carrier.

The present invention provides a composition comprising paroxetine or a pharmaceutically acceptable derivative thereof adsorbed on or absorbed by a pharmaceutically acceptable solid carrier, and the use of the composition as a therapeutic agent or for the manufacture of a medicament.

By this invention paroxetine may be obtained as a free-flowing powder that can be used directly (for example by direct compression into tablet form) or with further compounding ingredients in therapy.

The paroxetine used in carrying out this invention is preferably paroxetine free base, but may alternatively be a pharmaceutically acceptable derivative such as a salt, more especially the hydrochloride.

The composition of this invention is simply obtained by combining a solution of paroxetine with a suitable adsorbent or absorbent material and evaporating the solvent, for example by spray drying. The solvent is suitably toluene, ethanol, acetone, propan-2-ol, or ethyl acetate, or any other suitable solvent or mixture of solvents, in a paroxetine concentration of between 1 and 20%, more preferably between 1 and 4%.

Alternatively an oil obtained by removal of solvent from a solution may be blended with a solid adsorbent or absorbent material.

Typically the material selected as carrier for the paroxetine is an excipient suitable for tablet formation or as a fill material for gelatine capsules, such as cyclodextrin (beta and/or gamma), porous silicates, starch, lactose or calcium phosphate, silica, sorbitol, maltodextrin, microcrystalline or powdered cellulose, sodium or calcium carboxymethylcellulose, calcium carbonate, kaolin, magnesium aluminum silicate. Additionally, soluble excipients such as magnesium stearate may form part of the solution phase.

Advantageously the carrier is one that also has a taste-masking effect, for example ion-exchange resins.

A solution of paroxetine free base may be prepared by addition of a base such as triethylamine to a solution of a crystalline paroxetine salt especially the hydrochloride or acetate. Alternatively the solution may be prepared by basifying a solution of an amorphous paroxetine hydrochloride or a crystalline anhydrate or hydrated form of paroxetine hydrochloride.

The preparation of the free base and the maleic acid salt are described in Example 2 of U.S. Pat. No. 4,007,196. The acetate salt may also be used as a starting material. Procedures for forming salts are described in EP-A-0223403.

Additionally the paroxetine free base may be prepared as a solution or oil by adding a base such as potassium hydroxide to a solution of a N-protected paroxetine compound such as N-phenoxycarbonyl paroxetine.

The composition of this invention comprising paroxetine adsorbed on or absorbed by a solid carrier may be formulated with or without conventional excipients for tablet formation or used as a powder fill for capsules.

The amount of paroxetine used is adjusted such that in a single unit dose there is a therapeutically effective amount of paroxetine. Preferably the unit dose contains from 10 to 100 mg paroxetine (as measured in terms of the free base). More preferable the amount of paroxetine in a unit dose is 10 mg, 20 mg, 30 mg, 40 mg or 50 mg. The most preferred amount of paroxetine in a unit dose is 20 mg.

Therapeutic uses of the paroxetine product of this invention include treatment of: alcoholism, anxiety, depression, obsessive compulsive disorder, panic disorder, chronic pain, obesity, senile dementia, migraine, bulimia, anorexia, social phobia, pre-menstrual syndrome (PMS), adolescent depression, trichotillomania, dysthymia, and substance abuse, referred to below as "the disorders".

Accordingly, the present invention also provides:

a pharmaceutical composition for treatment or prophylaxis of the disorders comprising paroxetine or a pharmaceutically acceptable derivative thereof adsorbed on or absorbed by a solid carrier and, optionally, at least one further pharmaceutically acceptable excipient;

the use of paroxetine or a pharmaceutically acceptable derivative thereof adsorbed on or absorbed by a solid carrier to manufacture a medicament for the treatment or prophylaxis of the disorders; and a method of treating the disorders which comprises administering an effective or prophylactic amount of paroxetine or a pharmaceutically acceptable derivative thereof adsorbed on or absorbed by a solid carrier to a person suffering from one or more of the disorders.

The invention is illustrated by the following Examples:

EXAMPLE 1

Preparation of Tablet Premix Containing Paroxetine Free Base.

A mixture of dibasic calcium phosphate dihydrate (408 g), hydroxypropylmethyl cellulose (25 g) and sodium starch glycollate (25 g) was blended in a key granulator for 3 minutes at a stir rate of 240 r.p.m. and an impeller rate of 3000 r.p.m. Purified water (57 ml) was added at a rate of approximately 4 ml/minute for 13.5 minutes while the key granulator was set at a stir rate of 240 r.p.m. and the impeller rate was set at 1500 r.p.m. The mixture was stirred for a further 1 minute, and the resulting granules dried in an air oven at 50° C. for 3 hours.

A portion of the granules prepared above (50 g) was added to a solution of paroxetine free base (2.0 g) in propan-2-ol (50 ml) and the resulting slurry dried under vacuum with agitation at 50° C.

This product is suitable for direct compression into tablets containing 10, 20, or 30 mg paroxetine.

EXAMPLE 2
Preparation of a Solid Supported Form of Paroxetine Free Base.

A stirred mixture of N-phenoxycarbonyl paroxetine (50.0 g), potassium hydroxide (45.0 g) and toluene (750 ml) was heated to reflux under a nitrogen atmosphere for 3 hours. After allowing the mixture to cool to room temperature, distilled water (500 ml) was added and the mixture stirred for 30 minutes. The organic layer was separated, dried over magnesium sulfate and concentrated to a total volume of 85 ml.

Toluene (100 ml) was added to an aliquot of the solution of paroxetine free amine in toluene (0.43 g/ml) (2.4 ml) and to this solution was added Celite (25.0 g) and the mixture stirred for 5 minutes. Solvent was removed under reduced pressure (water bath 55° C.) to afford the Celite supported paroxetine free amine as a free moving powdery solid (26.0 g).

This product may be mixed with additional excipients and compressed into tablets or added directly to capsule shells to make a product containing a therapeutic dose of paroxetine.

EXAMPLE 3
Spray Drying of Paroxetine Hydrochloride Solution onto a Suspended Carrier Material.

Anhydrous paroxetine hydrochloride (60 g) was dissolved in anhydrous ethanol (725 ml) and the clear solution slurried with maltodextrin DE4-6 (506 g). The uniform suspension was spray-dried in a Niro Mobile Minor (TM) closed cycle spray dryer using nitrogen as the process gas, a rotary atomiser wheel spinning at 27,000 r.p.m. (alternatively a co-current or fountain two-fluid nozzle could be used), an inlet temperature of 96–104 C. and outlet temperature of 44–50 C. at a feed rate of 4.1 kg per hour. A white free-flowing product was recovered (490 g) which was found to have a mean particle size of 84 microns.

EXAMPLE 4
Preparation of Tablet Pre-mix Containing Paroxetine Hydrochloride.

A mixture of dibasic calcium phosphate dihydrate (408 g), hydroxypropylmethyl cellulose (25 g) and sodium starch glycollate (25 g) was blended in a key granulator for 3 minutes at a stir rate of 240 r.p.m. and an impeller rate of 3000 r.p.m. Purified water (57 ml) was added at a rate of approximately 4 ml/minute for 13.5 minutes while the key granulator was set at a stir rate of 240 r.p.m. and the impeller rate was set at 1500 r.p.m. The mixture was stirred for a further 1 minute, and the resulting granules dried in an air oven at 50° C. for 3 hours.

A solution of paroxetine hydrochloride hemihydrate (2.0 g) in ethanol (100 ml) was added to the granules prepared above (50 g) and the slurry dried under vacuum at 50° C.

EXAMPLE 5
Preparation of Tablet Pre-mix Containing Paroxetine Hydrochloride.

A solution of paroxetine hydrochloride hemihydrate (2.0 g) in ethanol (150 ml) was added to celite (50 g), the mixture stirred and the slurry dried under vacuum at 50° C. to afford a free moving powdery solid, suitable for use as a component of a tablet or capsule formulation.

EXAMPLE 6
Preparation of Tablet Pre-Mix Containing Paroxetine Hydrochloride.

A stirred mixture of N-phenoxycarbonyl paroxetine (50.0 g), potassium hydroxide (45.0 g) and toluene (750 ml) was heated to reflux under a nitrogen atmosphere for 3 hours. After allowing the mixture to cool to room temperature, distilled water (500 ml) was added and the mixture stirred for 30 minutes. The organic layer was separated, dried over magnesium sulphate and filtered. An aliquot of this solution of paroxetine free amine in toluene [0.048 g/ml] (21.0 ml) was diluted with a further 30 ml of toluene and heated to 60° C. Concentrated hydrochloric acid (0.34 ml) was added and the mixture stirred for 10 minutes. Tablet granules (25.0 g), prepared as in Example 4, were added and the mixture stirred at 60° C. for 5 minutes. Solvent was removed under reduced pressure at 70° C. to afford a mobile powdery solid (26.0 g).

EXAMPLE 7
Preparation of Tablet Pre-mix Containing Paroxetine Hydrochloride.

Concentrated hydrochloric acid (0.34 ml) was added to a stirred solution of paroxetine acetate (1.18 g) in toluene (50 ml) at 60° C. and the mixture stirred for 10 minutes. Tablet granules (25.0 g), prepared as in Example 4, were added and the mixture stirred at 60° C. for 5 minutes. Solvent was removed under reduced pressure at 70° C. to afford a free flowing powdery solid (26.0 g).

What is claimed is:

1. A process for the preparation of a pharmaceutical composition containing paroxetine or a pharmaceutically acceptable salt thereof which process comprises combining a solution of paroxetine or a pharmaceutically acceptable salt thereof with an adsorbent material and evaporating the solvent, wherein the absorbent material is calcium phosphate.

* * * * *